(12) United States Patent
Haberhausen et al.

(10) Patent No.: US 6,248,522 B1
(45) Date of Patent: Jun. 19, 2001

(54) REDUCTION OF CROSS-CONTAMINATIONS IN NUCLEIC ACID AMPLIFICATIONS

(75) Inventors: Gerd Haberhausen, Iffeldorf; Stephan Jäger; Harald Sobek, both of Penzberg, all of (DE)

(73) Assignee: Roche Diagnostics GmbH, Mannheim (DE)

(*) Notice: Subject to any disclaimer, the term of this patent is extended or adjusted under 35 U.S.C. 154(b) by 0 days.

(21) Appl. No.: 09/136,959

(22) Filed: Aug. 20, 1998

(30) Foreign Application Priority Data

Aug. 20, 1997 (DE) .............................. 197 36 062

(51) Int. Cl.[7] .................................................... C12Q 1/68
(52) U.S. Cl. .................... 435/6; 435/91.1; 435/91.2; 536/23.1; 536/23.5; 536/23.6
(58) Field of Search .................... 435/6, 91.2; 536/23.1, 536/23.5, 23.6

(56) References Cited

U.S. PATENT DOCUMENTS 5,418,149 * 5/1995 Gelfland et al. .................... 435/91.2

* cited by examiner

Primary Examiner—Kenneth R. Horlick
Assistant Examiner—Janell E. Taylor
(74) Attorney, Agent, or Firm—Arent Fox Kintner Plotkin Kahn

(57) ABSTRACT

The invention concerns a method for the amplification of nucleic acids using a reagent which prevents reactivation of degradation enzymes. This enables a simpler prevention of contaminations.

34 Claims, 2 Drawing Sheets

SEQUENCE LISTING

<160> NUMBER OF SEQ ID NOS: 6

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence:Primer

<400> SEQUENCE: 1
cctcttcccc agaacaataa gaacac                                          26

<210> SEQ ID NO 2
<211> LENGTH: 25
<212> TYPE: DNA
<213> ORGANISM: Artificial Sequence
<220> FEATURE:
<221> NAME/KEY: misc_feature
<222> LOCATION: (1)
<223> OTHER INFORMATION: Labeled with Biotin
<223> OTHER INFORMATION: Description of Artificial Sequence:Primer

<400> SEQUENCE: 2
gggattcctg taacaacaag tcagg                                           25

<210> SEQ ID NO 3
<211> LENGTH: 20
<212> TYPE: DNA
<213> ORGANISM: Artificial Sequence
<220> FEATURE:
<221> NAME/KEY: misc_feature
<222> LOCATION: (1)
<223> OTHER INFORMATION: Labeled with Ruthenium
<223> OTHER INFORMATION: Description of Artificial Sequence:Primer

<400> SEQUENCE: 3
catagcacta tagaactctg                                                 20

<210> SEQ ID NO 4
<211> LENGTH: 30
<212> TYPE: DNA
<213> ORGANISM: Artificial Sequence
<220> FEATURE:

-continued

```
<223> OTHER INFORMATION: Description of Artificial Sequence:Primer

<400> SEQUENCE: 4
agttggagga catcaagcag ccatgcaaat                                  30

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 5
tgctatgtca gttcccttg gttctct                                      27

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 6
atcaatgagg aagctgcaga                                             20
```

REDUCTION OF CROSS-CONTAMINATIONS IN NUCLEIC ACID AMPLIFICATIONS

The invention concerns methods for amplifying nucleic acids, methods for detecting nucleic acids with the aid of these amplification methods, the use of lauroyl sarcosine to prevent the reactivation of uracil-N-glycosilase as well as a reagent and a reagent kit for carrying out this method.

Since the introduction of methods for amplifying nucleic acids (e.g. the polymerase chain reaction (PCR) as described in U.S. Pat. No. 4,683,202) into nucleic acid diagnostics, a whole series of analytes have become analytically detectable for the first time. These methods are even able to amplify analyte nucleic acids, e.g. of HCV, that are present in the smallest concentrations to such an extent that they become accessible to those nucleic acid tests which have previously been restricted to highly concentrated analytes. However, over time it has turned out that the laboratories in which the amplifications were carried out have in the meantime already become so strongly contaminated with the amplified nucleic acids that tests in samples which in fact do not contain the low concentrated nucleic acid at all lead to false-positive results since the samples have become contaminated by the environment with nucleic acids from previous amplifications (cross-contaminations). The high sensitivity of the amplification-based nucleic acid tests enables the detection of even the slightest contaminations and hence simulates the presence of the analyte in the sample (false-positive results).

A method for stabilizing alkaline solutions containing nucleic acids with anionic, non-ionic and zwitterionic detergents is described in EP-B-0 566 050.

EP-A-0 401 037 describes a method which partially remedies the described deficiency. In this method mononucleotides that are not naturally present in the nucleic acid to be detected are incorporated during the amplification into the amplificate of each analyte nucleic acid. Before a subsequent amplification is carried out, the sample together with the reagents used are subjected to a pretreatment in which all imported amplificates from earlier amplifications are enzymatically degraded. Uracil-N-glycosilase (UNG) is an example of a degradation reagent and dUTP is an example of a modified building block for the amplificates. An alternative method utilizes primers containing uracil instead of mononucleotides containing uracil. Such a method in which the primer binding sites are degraded on amplificates generated earlier is described in EP-A-0 415 755.

The mechanism of this decontamination method is based on the specific recognition of uracil-containing amplificates which are degraded by the enzyme. In the preparation of the amplification reaction UNG is added to the sample and usually already together with the master mix which contains all reagents necessary for the amplification. The aforementioned degradation reaction takes place in a brief incubation step before the subsequent amplification. If the reaction mixture is subsequently heated to a temperature above ca. 40° C., then UNG is inactivated. This is necessary to ensure that the UNG does not degrade the newly synthesized DNA which accumulates during the course of the amplification.

If, however, the detection reaction does not directly follow the amplification, the denatured enzyme refolds and hence regains its activity (BioTechniques 13, 181–183, 1992). This can lead to false-negative test results. Various methods have previously been used to prevent the UNG reactivation. In a first variant the amplificates are stored at higher temperatures (e.g. >50° C.). However, this requires either an additional thermostated instrument or the thermocycler position is blocked by the reaction vessel until the test is continued. On the other hand a temperature-dependent degradation of the amplificate also occurs over time under these conditions. In a further variant the amplificates are stored at low temperatures (e.g. 4° C.). This variant also leads to additional hardware requirements and thus to increased costs. In a third variant a stop solution (usually NaOH) is added to the reaction solution after carrying out the amplification. However, adding a stop solution by pipette reduces convenience for the operator and is invariably linked with an opening of the reaction tube whether this is carried out manually or automatically. However, the risk of contamination also considerably increases with each additional working step especially after amplification.

Therefore the object of the present invention was to completely or partially avoid the disadvantages of the prior art and in particular to provide a more simple amplification method with a reduced risk of contamination.

The invention concerns a method for amplifying nucleic acids in a sample comprising the steps
treating the sample with an enzyme under conditions in which products from the amplifications of nucleic acids of other samples are enzymatically degraded,
inactivating the enzyme and
treating the sample under conditions in which the nucleic acids are amplified,
wherein the amplification is carried out in the presence of a reagent that prevents reactivation of the enzyme.

The invention also concerns a reagent that can be used in the above method and the use of detergents in methods for the amplification of nucleic acids.

Figure 1:
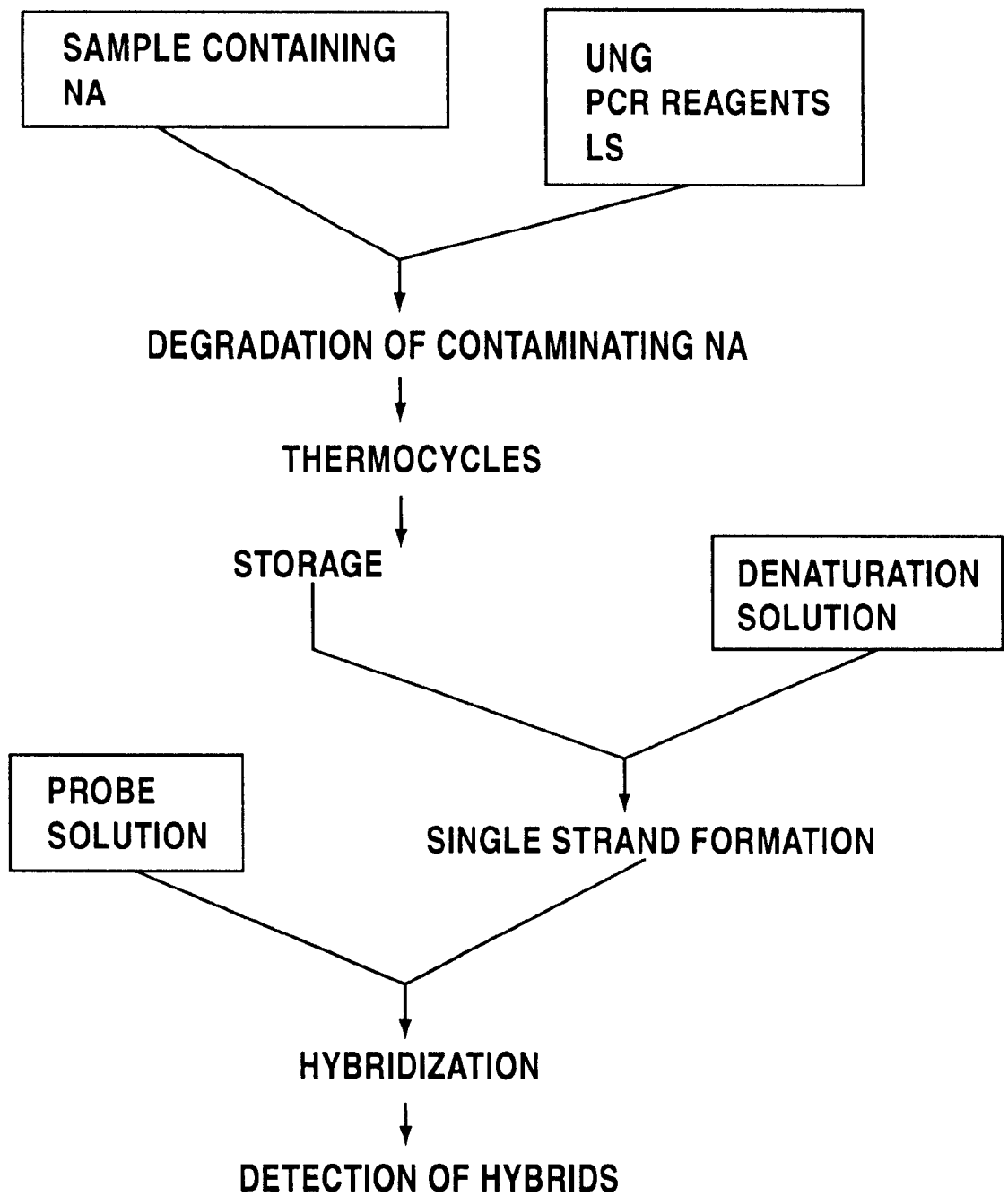
FIG. 1 shows a diagram of an example of a detection method in which the reagent is already added to the sample before amplification.

A detergent within the sense of the present invention is understood as a surface-active substance which can in principle have an anionic, cationic, ampholytic or non-ionic composition. Anionic detergents are preferred.

The essence of the present invention is the recognition that it is possible to suppress the reactivation of degradation enzymes after an amplification by already adding a reagent before the amplification. A person skilled in the art would not have expected that there could be a reagent which prevents the reactivation of the enzyme but does not have a significant negative influence on the activity of the native enzyme.

The amplification method according to the invention uses a sample which contains the nucleic acid to be amplified. The method according to the invention is usually used analytically which is why the nucleic acid present in the sample is also called analyte nucleic acid. However, there are also other ways of using the nucleic acids according to the invention e.g. for subsequent recombinant cloning or sequencing. Analyte nucleic acids are understood as nucleic acids of any origin such as nucleic acids of viroid, viral, bacterial or cellular origin. They can be present in solution, suspension and also fixed to solid bodies or in cell-containing media, cell smears, fixed cells, tissue sections or fixed organisms. The nucleic acids are preferably present in solution.

If the nucleic acid is not yet accessible, it is advantageously made available using appropriate reagents. In this connection pH changes (alkaline), heat, repeating extreme temperature changes (freezing/thawing), changing the physiological growth conditions (osmotic pressure), the action of detergents, chaotropic salts or enzymes (e.g. proteases, lipases), alone or in combination can contribute to the release of the nucleic acids.

In a first essential reaction of the method according to the invention contaminating nucleic acids are enzymatically degraded. Methods which accomplish this are known from the prior art e.g. from EP-A-0 401 037 and EP-A-0 415 755 to the complete contents of which reference is herewith made. For this the conditions that are necessary for the degradation are adjusted in the sample by adding reagents which contain the enzyme. The addition can in principle be carried out individually, but also together with other reagents. All enzymes can be used as the degrading enzyme which have the effect that nucleic acids that are not intended to be the target of the actual detection or the actual amplification are no longer available as a template for the amplification but do not significantly impair the nucleic acid to be amplified from the sample. These for example include enzymes which recognize properties or modifications that are characteristic for the amplification products e.g. the incorporation of special mononucleotides or oligonucleotides. An outstanding example of such an enzyme is uracil-N-glycosilase which recognizes uracil incorporated into the amplificates and degrades all U-containing nucleic acids to such an extent that they are no longer available as a template for the subsequent amplification. For this dUTP or a U-containing primer is used in the amplification reaction instead of or in addition to the normal dTTP or the corresponding oligonucleotide. As a result amplificates from other sources than the actual sample can be chemically differentiated from the nucleic acids to be amplified of the actual sample.

The enzymatic degradation reaction is carried out until it is estimated that cross-contaminating nucleic acids are no longer present in the sample. Afterwards the enzyme is inactivated. This can in turn be achieved in various ways but thermal inactivation is preferred since the reaction vessel does not have to be opened for this. For this the reaction mixture is heated to a temperature at which the enzyme is inactivated i.e. that it is changed to such an extent, presumably by alterations of its spatial arrangement, that the enzymatic activity is lost. If heat-labile UNG is used, a temperature of 50° C., preferably of 40° C. to 96° C. is adequate for this. The heat-stable UNG requires a higher temperature for inactivation. In the thermal amplification methods preferred according to the invention the inactivation can take place in the first heat step of the amplification method thus obviating a separate step. In this case it is preferred that the reagents required for the amplification i.e. in particular the (mono)nucleoside triphosphates, the polymers, the primers and possibly buffers are already added to the sample together with the degradation enzyme or shortly before or after addition of the degradation enzyme. It is particularly preferable to add the reagents required for the amplification, for the degradation and for the inactivation as a mixture or solution. This saves working steps and lowers the active and passive risk of contamination.

An amplification within the sense of the invention means all in vitro methods for multiplying nucleic acids or parts thereof and especially methods based on thermocycling. PCR is a particularly preferred amplification method. Full reference is herewith made to the disclosure in U.S. Pat. No. 4,683,202. Those amplification methods are especially preferred in which extension products of a primer are formed using the nucleic acid to be amplified as a template nucleic acid catalysed by a DNA polymerase, preferably a thermostable polymerase, especially preferably T.aq (DNA) or T.th (RNA) polymerase, which in turn serve as a template nucleic acid for the extension of a primer. Parts of the nucleic acid are theoretically amplified exponentially by cyclic denaturation of the double strands formed, hybridizing primers to them and extending the primers.

Nucleoside triphosphates (NTP) are ribo (rNTP) or deoxy-ribonucleoside triphosphates (dNTP). They can be labelled or unlabelled.

A template nucleic acid is a nucleic acid to which an essentially complementary nucleic acid strand is newly formed. With regard to the sequence information the template nucleic acid serves as a template for the transcription.

The reactions preferably take place in a plastic vessel. In particular those vessels can be used for this which are normally used in standard thermocyclers as amplification vessels. Examples are vessels of polystyrene, polyethylene or Luran.

The reagent that prevents reactivation can in principle be added to the sample in any step of the reaction but advantageously before the enzyme has had the opportunity to reactivate which means at the latest after completion of the amplification; since the reactivation occurs at different rates depending on the storage temperature of the reaction mixture after amplification, an early addition is more appropriate at higher temperatures than at lower temperatures. Waiting lowers the yield of amplificates since the enzyme starts again to degrade the nucleic acids that have just been amplified.

However, the reagent is preferably already added to the sample together with the degrading enzyme.

Substances with a hydrophobic group, especially detergents, have proven to be useful as a reagent. It was found that the refolding of the enzyme can be substantially suppressed by such substances. This applies especially to detergents with a pronounced hydrophobic moiety of ca. 5 to 30 carbon atoms e.g. a fatty acid residue such as preferably a lauroyl residue or N-acyl-amino acids. Attachment of the hydrophobic residues presumably impedes restructuring. Additional reagents that can be used are for example LDS (lithium dodecyl sulfate) or SDS (sodium dodecyl sulfate) although these have the problem of a low solubility at low temperatures. The class of anionic detergents is particularly suitable within the sense of the invention and in particular lauroyl sarcosine.

If the reagent should be present already during the amplification care must be taken that the reagent does not significantly impair the activity of the polymerase. This can be found out by a person skilled in the art from the group of the above mentioned reagents by simple amplification experiments in the presence of the selected reagent. A slightly reduced amplification efficiency can also be compensated by adding a little more polymerase.

The concentration of the reagent also depends on the reagent itself so that it is very difficult to give details that apply to the whole group. For N-lauroyl sarcosine (LS) it has for example proven to be expedient to select the concentration in the range between 0.01 and 0.1% by weight (w/v), particularly preferably 0.04% and 0.05% (final concentration in the PCR mixture).

The method according to the invention has the advantage that the resulting reaction mixtures do not have to be immediately used for the detection after amplification but can also be stored for some time at room temperature without a significant degradation of the amplification products. A separate addition of reagents is not necessary.

The amplification method according to the invention can be used to produce adequate amounts of detectable nucleic acids. The amplificates formed according to the invention can then be detected in the test procedure in a generally known manner. In the process detectable groups such as fluorescent labels can also already be incorporated into the amplificates during the amplification. The amplificates are preferably hybridized with a labelled probe, captured on a solid phase, optionally freed from a possible excess of labelled components and detected on the solid phase on the basis of the label that is present. Numerous formats for such tests are known e.g. a format as described in EP-A-0 324 474.

In a particular preferred embodiment (cf. FIG. 1) a reagent containing UNG, LS, mononucleoside triphosphate mixture (also containing dUTP), T.th polymerase and HIV-specific biotin-labelled primers are added to the sample e.g. a serum after sample preparation. The vessel is closed and incubated for a period. Then the vessel is transferred to a thermocycler and heated as required for the thermocycles. Afterwards the vessel is opened, the nucleic acid is denatured and subsequently a ruthenium-labelled detector probe as well as a suspension of streptavidin-coated magnetic beads are added. After mixing, the mixture is transferred to a measuring cell for an electrochemiluminescence measurement. The measured signal is an indication of the amount or the presence of HIV nucleic acids in the sample.

The invention also concerns a reagent kit for the amplification of nucleic acids containing, in one or several containers, reagents for the amplification of nucleic acids, a nucleic acid-degrading enzyme as well as a reagent preventing the reactivation of the enzyme.

The invention additionally concerns a reagent for the amplification of nucleic acids containing in a solution
- at least one reagent selected from the group comprising nucleoside triphosphates, primers, polymerase,
- a nucleic acid-degrading enzyme and
- a reagent that prevents reactivation of the enzyme that degrades the nucleic acid.

An additional subject matter of the invention is the use of lauroyl sarcosine to prevent the reactivation of uracil-N-glycosilase.

Within the scope of the invention it was also found that it is not necessary to already add the reagent preventing reactivation of the enzyme before amplification of the sample. The addition is not really necessary until the enzyme has had the opportunity to reactivate i.e. e.g. cooling below the temperature at which refolding takes place. This means that the reagent can also be added after the amplification has been carried out. In this case as well as in the previously described embodiment it is preferable to use a reagent which does not itself deactivate the enzyme activity but prevents reactivation from a non-active state. Substances with a hydrophobic group, in particular detergents, as described above are particularly suitable.

Furthermore it was also found in these investigations that methods for the detection of nucleic acids comprising the steps of in vitro production of numerous copies of a partial region of the nucleic acid and detection of the copies as a measure of the presence or the amount of the nucleic acid to be detected can be improved by adding a detergent to the solution containing the copies before the detection. The detergent leads to a reduction of undesired side reactions of DNA polymerases at low temperatures e.g. filling up reactions on single-stranded templates. These side reactions can considerably impair the performance of the test procedure.

A special subject matter is a method for the amplification of nucleic acids in a sample comprising the steps of treating the sample with an enzyme under conditions in which products from the amplifications of nucleic acids from other samples are enzymatically degraded, inactivating the enzyme and treating the sample under conditions in which the nucleic acids are amplified wherein, after amplification, a reagent is added to the sample which does not impair the enzyme activity of the active enzyme but prevents the reactivation of the enzyme.

Figure 2:
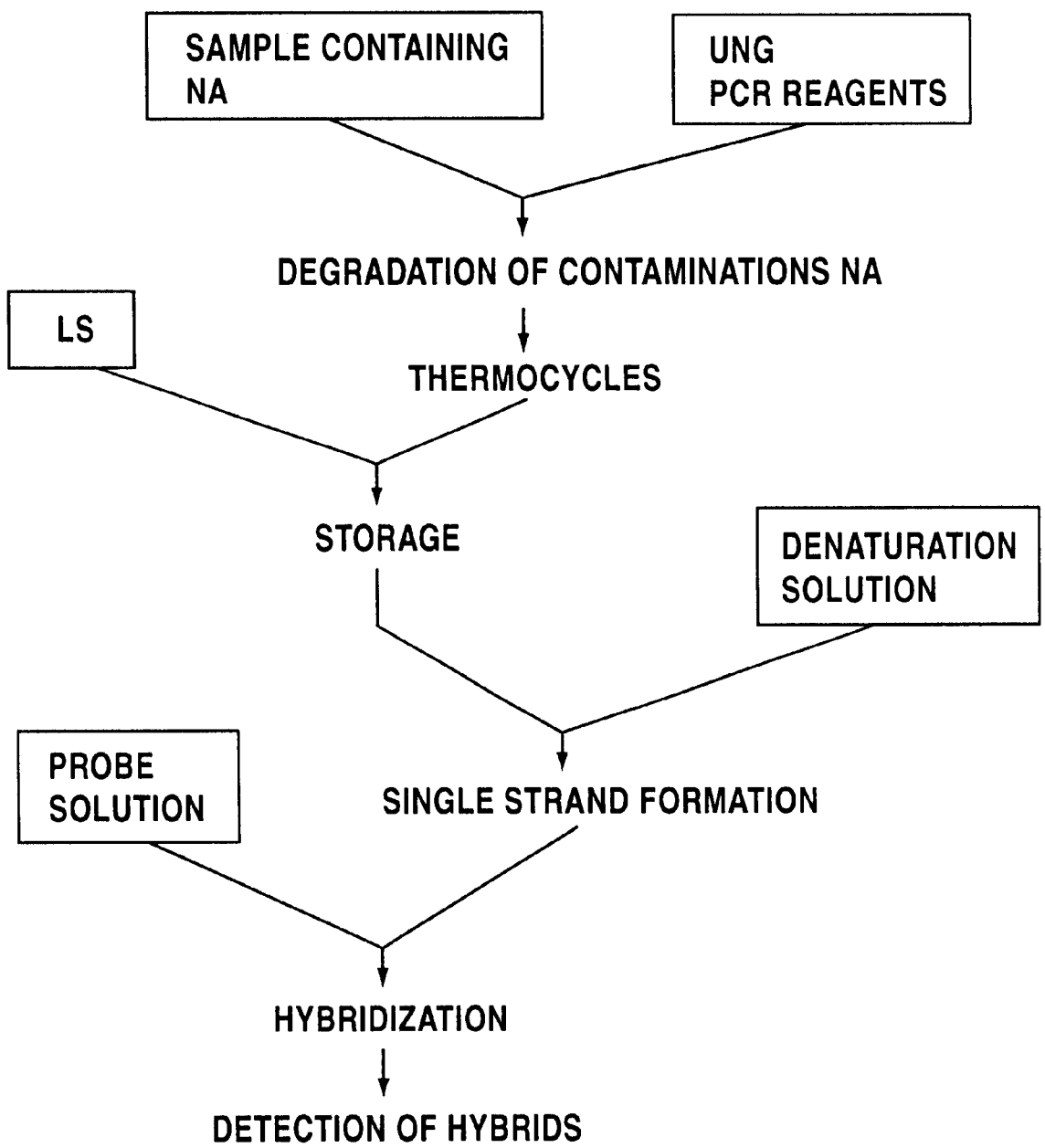
FIG. 2 shows a diagram of a method in which the reagent is added after amplification.

Such a method is shown schematically in FIG. 2. In this embodiment the sample which contains the nucleic acid (NA) is firstly contacted with the UNG and the PCR reagents. This results in the degradation of contaminating nucleic acids. Subsequently the reaction mixture is subjected to thermocycles. After amplification the reagent (in this case lauroyl sarcosine, LS) is added. The resulting mixture can now be stored until it is intended to add a denaturing solution to the single strand mixture of amplificates. Afterwards a solution containing a detector probe is added, hybridization conditions are set and the hybrids are optionally detected.

It is intended to further elucidate the invention by the following examples:

EXAMPLE 1

Influence of LS on the amplification efficiency and UNG reactivation when added to the master mix using Chlamydia as an example (DNA-PCR with Taq polymerase):

| Reagents | Final concentration in the master mix |
|---|---|
| 10 x PCR buffer | 1 x |
| $MgCl_2$ | 2.5 mM |
| Taq polymerase | 5 u |
| dNTP mix | 200 $\mu$M (dATP, dCTP, dGTP)/600 $\mu$M (dUTP) |
| UNG | 2 u |

-continued

| Reagents | Final concentration in the master mix |
|---|---|
| LS | 0.05% (optional) |
| forward primer | 0.3 µM (5'-cctcttccccagaacaataagaacac-3', SEQ ID NO. 1) |
| reverse primer | 0.3 µM (5'-bio-gggattcctgtaacaacaagtcagg-3', SEQ ID NO. 2) |

LS: N-lauroyl sarcosine (Applichem, GER, order No. A1163) The amplification was carried out according to the following cycler protocol:

| 10 min | 37° C. | decontamination by UNG |
| 5 min | 95° C. | denaturation |
| 1 min | 60° C. | primer annealing and elongation |
| 30 sec | 95° C. | 29 cycles of amplification |
| 1 min | 60° C. | |

$10^1$ and $10^2$ copies of Chlamydia plasmid were amplified in multiple determinations. The amplification was carried out in each case with and without LS (control) in the master mix. After amplification all samples were measured ($t_0$), subsequently incubated for 3 hours at 30° C. ($t_{3h}$) and then measured again (ECL detection, Elecsys®1010, Boehringer Mannheim GmbH). A ruthenium-labelled DNA probe was used for the hybridization (5'Ru-catagcactatagaactctg-3', SEQ ID NO.3).
Result:

| | without LS | | with LS | |
|---|---|---|---|---|
| Chlamydia plasmid | $t_0$ | $t_{3h}$ | $t_0$ | $t_{3h}$ |
| $10^2$ copies | 377 | 58 | 401 | 385 |
| $10^2$ copies | 342 | 61 | 286 | 253 |
| $10^2$ copies | 409 | 49 | 278 | 270 |
| $10^2$ copies | 441 | 42 | 289 | 301 |
| $10^2$ copies | 279 | 53 | 421 | 399 |
| $10^2$ copies | 313 | 37 | 345 | 328 |
| $10^2$ copies | 446 | 68 | 499 | 479 |
| $10^2$ copies | 364 | 59 | 331 | 296 |
| $10^1$ copies | 13 | 9 | 51 | 29 |
| $10^1$ copies | 43 | 9 | 16 | 12 |
| $10^1$ copies | 15 | 8 | 18 | 15 |
| $10^1$ copies | 19 | 8 | 99 | 61 |
| $10^1$ copies | 23 | 9 | 207 | 136 |
| $10^1$ copies | 25 | 8 | 51 | 73 |
| $10^1$ copies | 43 | 8 | 37 | 22 |
| $10^1$ copies | 48 | 9 | 34 | 19 |
| $10^1$ copies | 22 | 7 | 30 | 19 |
| $10^1$ copies | 37 | 9 | 56 | 35 |

The results show that LS has hardly any influence on the amplification efficiency of the Taq polymerase. At the same copy numbers the signals are also of the same order of magnitude after detection independently of whether the amplification was carried out in the presence of or without LS.

On the other hand LS has a very positive effect on the amplificate stability especially at low copy numbers. If one defines a value under which individual samples are found to be negative (cut off), then with the low copy number of 10 copies as an example one finds that firstly all samples are classified as positive, but after 3 h incubation (30° C.) all were found to be negative. This effect is completely avoided by adding LS to the reaction mixture. This considerably improves the reliability of the result!

EXAMPLE 2

Influence of LS on the decontamination efficiency:

In order to test the decontamination efficiency, firstly an artificial contamination series of $10^1$ to $10^6$ copies of a uracil-containing amplificate (substrate for the UNG) was prepared. This was subsequently amplified using the aforementioned master mix and PCR protocol and the results were examined with regard to decontamination/reamplification.

| Chlamydia-dUTP amplificate | without UNG | with UNG with LS | with UNG without LS |
|---|---|---|---|
| $10^1$ copies | 4 | 4 | 4 |
| $10^2$ copies | 9 | 4 | 4 |
| $10^3$ copies | 402 | 9 | 6 |
| $10^4$ copies | 912 | 30 | 62 |
| $10^5$ copies | 3091 | 145 | 221 |
| $10^6$ copies | 4243 | 638 | 783 |

LS has no influence on the decontamination efficiency of UNG at the start of the amplification. In both cases (+/−LS) there is a decontamination of at least $10^3$ copies of amplificate.

EXAMPLE 3

Influence of LS on the signal stability when added after PCR using HIV as an example (RNA-PCR with Tth polymerase):

| Reagents | Final concentration in the master mix |
|---|---|
| 5 x RT-PCR buffer | 1 x |
| MnOAc | 1.25 mM |
| Tth polymerase | 15 u |
| dNTP mix | 200 µM (dATP, dCTP, dGTP)/600 µM (dUTP) |
| UNG | 2 u |
| forw. primer SK462 | 0.2 µM (AGTTGGAGGACATCAAGCAGCCATGCAAAT; SEQ ID NO. 4) |
| rev. primer SK431-bio | 0.2 µM (TGCTATGTCAGTTCCCCTTGGTTCTCT; SEQ ID NO. 5) |

The amplification was carried out according to the following cycler protool:

| | 10 min | 37° C. | decontamination by UNG |
| | 30 min | 60° C. | reverse transcription |
| 4 cycles: | 10 sec | 95° C. | denaturation |
| | 10 sec | 55° C. | primer annealing |
| | 10 sec | 72° C. | elongation |
| 26 cycles: | 10 sec | 90° C. | denaturation |
| | 10 sec | 60° C. | primer annealing |
| | 10 sec | 72° C. | elongation |

$10^2$, $10^4$ and $10^5$ copies of HIV-RNA standard were amplified in multiple determinations. After the amplification all samples were firstly divided and measured ($t_0$), subsequently half of the samples were stopped with 0.05% LS (w/v, final concentration) and all samples were incubated for 3 h at 30° C. (t3h) and then measured again (ECL detection, Flash Symu). A ruthenium-labelled DNA probe was used for the hybridization. (SK102b, ATCAATGAGGAAGCTGCAGA, SEQ ID NO.6).

Result:

| Chlamydia plasmid | without LS | | with LS | |
|---|---|---|---|---|
| | $t_0$ | $t_{3h}$ | $t_0$ | $t_{3h}$ |
| $10^5$ copies | 3204 | 2898 | 3167 | 3162 |
| $10^5$ copies | 3095 | 2924 | 2987 | 3033 |
| $10^5$ copies | 3003 | 2992 | 3053 | 3053 |
| $10^5$ copies | 3118 | 2944 | 3091 | 3056 |
| $10^4$ copies | 1307 | 1105 | 1311 | 1300 |
| $10^4$ copies | 1310 | 1177 | 1287 | 1249 |
| $10^4$ copies | 1295 | 1120 | 1284 | 1328 |
| $10^4$ copies | 1317 | 1111 | 1350 | 1284 |
| $10^2$ copies | 205 | 189 | 204 | 200 |
| $10^2$ copies | 207 | 195 | 201 | 203 |
| $10^2$ copies | 208 | 194 | 205 | 202 |
| $10^2$ copies | 200 | 188 | 199 | 200 |

The results show that the incubation of the amplificates without LS leads to a weak but significant decrease in the signal. This is completely avoided by adding N-lauroyl sarcosine.

What is claimed is:

1. A method for amplifying a target nucleic acid in a sample while avoiding amplification of any contaminating nucleic acid amplification product present in the sample, the method comprising the steps of:
   (a) combining the sample with an active enzyme which degrades any contaminating nucleic acid amplification product present in the sample without degrading the target nucleic acid;
   (b) inactivating the enzyme;
   (c) amplifying the target nucleic acid; and
   (d) combining the sample with a first reagent which prevents reactivation of the inactivated enzyme from step (b) while avoiding any significant chemical inactivation of the active enzyme from step (a),
thereby amplifying the target nucleic acid while avoiding amplification of the contaminating nucleic acid amplification product.

2. The method of claim 1, wherein the first reagent is combined with the sample before said amplifying step.

3. The method of claim 1, wherein the first reagent is combined with the sample after said amplifying step.

4. The method of claim 1, wherein the enzyme is uracil-N-glycosilase.

5. The method of claim 1, wherein the enzyme is thermally inactivated.

6. The method of claim 5, wherein said inactivating step and said amplifying step are carried out in a same step.

7. The method of claim 1, wherein amplification reagents for use in said amplifying step and the first reagent are combined with the sample before said amplifying step.

8. The method of claim 1, wherein amplification reagents for use in said amplifying step, the enzyme and the first reagent are combined with the sample before said amplifying step.

9. The method of claim 8, wherein the amplification reagents for use in said amplifying step, the enzyme and the first reagent are combined as a mixture with the sample.

10. The method of claim 1, wherein the enzyme and the first reagent are combined with the sample in a same step.

11. The method of claim 1, wherein the first reagent is a detergent having a hydrophobic residue.

12. The method of claim 11, wherein the hydrophobic residue comprises 5 to 30 carbon atoms.

13. The method of claim 12, wherein the hydrophobic residue comprises a fatty acid residue.

14. The method of claim 12, wherein the hydrophobic residue comprises a lauroyl residue or an N-acyl-amino acid.

15. The method of claim 1, wherein the first reagent comprises lithium dodecyl sulfate or sodium dodecyl sulfate.

16. The method of claim 1, wherein the first reagent comprises an anionic detergent.

17. The method of claim 16, wherein the anionic detergent comprises lauroyl sarcosine.

18. The method of claim 1, further comprising, after said amplifying step, detecting any amplification product produced in said amplifying step as an indication of the presence or the amount of the target nucleic acid in the sample.

19. A kit for amplifying a target nucleic acid in a sample while avoiding amplification of any contaminating nucleic acid amplification product present in the sample, the kit comprising, in one or several containers,
   amplification reagents for amplifying the target nucleic acid;
   an active enzyme which degrades any contaminating nucleic acid amplification product present in the sample without degrading the target nucleic acid; and
   a first reagent which prevents reactivation of the enzyme after the enzyme is inactivated while avoiding any significant chemical inactivation of the active enzyme.

20. A reagent solution for amplifying a target nucleic acid in a sample while avoiding amplification of any contaminating nucleic acid amplification product present in the sample, the reagent solution comprising at least one amplification reagent for amplifying the target nucleic acid, the at least one amplification reagent selected from the group consisting of a nucleoside triphosphate, a primer and a polymerase;

an active enzyme which degrades any contaminating nucleic acid amplification product present in the sample without degrading the target nucleic acid; and a first reagent which prevents reactivation of the enzyme after the enzyme is inactivated while avoiding any significant chemical inactivation of the active enzyme.

21. A method of preventing the reactivation of an inactivated uracil-N-glycosilase, the method comprising combining the inactivated uracil-N-glycosilase with a detergent having a hydrophobic residue.

22. The method of claim 21, wherein the hydrophobic residue comprises 5 to 30 carbon atoms.

23. The method of claim 22, wherein the hydrophobic residue comprises a fatty acid residue.

24. The method of claim 21, wherein the hydrophobic residue comprises a lauroyl residue or an N-acyl-amino acid.

25. The method of claim 21, wherein the reagent comprises lithium dodecyl sulfate or sodium dodecyl sulfate.

26. The method of claim 21, wherein the reagent comprises an anionic detergent.

27. The method of claim 26, wherein the anionic detergent comprises lauroyl sarcosine.

28. In a method for detecting a nucleic acid comprising the steps of in vitro producing in a solution a plurality of copies of a partial region of the nucleic acid and thereafter detecting the copies as an indication of the presence or amount of the nucleic acid, the improvement comprising, before said detecting step, combining with the solution a detergent having a hydrophobic residue, to reduce undesired side reactions of any DNA polymerase present in the solution.

29. The improvement of claim 28, wherein the hydrophobic residue comprises 5 to 30 carbon atoms.

30. The improvement of claim 29, wherein the hydrophobic residue comprises a fatty acid residue.

31. The improvement of claim 28, wherein the hydrophobic residue comprises a lauroyl residue or an N-acyl-amino acid.

32. The improvement of claim 28, wherein the detergent comprises lithium dodecyl sulfate or sodium dodecyl sulfate.

33. The improvement of claim 28, wherein the detergent comprises an anionic detergent.

34. The improvement of claim 33, wherein the anionic detergent comprises lauroyl sarcosine.

* * * * *